United States Patent [19]

Chen et al.

[11] Patent Number: 5,314,976
[45] Date of Patent: May 24, 1994

[54] PHOTO-RESPONSIVE CONDUCTIVE POLYMERS AND THE PROCESSES OF MAKING THE SAME

[75] Inventors: Show-An Chen, Hsinchu; Chien-Hsiun Liao, Feng Yuan, both of Taiwan

[73] Assignee: National Science Council, Taiwan

[21] Appl. No.: 103,676

[22] Filed: Aug. 10, 1993

Related U.S. Application Data

[62] Division of Ser. No. 867,460, Apr. 13, 1992, Pat. No. 5,272,234.

[51] Int. Cl.$^5$ .................. C08F 228/06; C08F 226/06; C08F 230/08; C08F 220/70
[52] U.S. Cl. .................................... 526/256; 526/258; 526/266; 526/279; 526/287; 526/297; 526/310; 526/313; 526/317.1
[58] Field of Search ............... 526/256, 258, 279, 287, 526/297, 310, 313, 317.1

[56] References Cited

PUBLICATIONS

R. Sugimoto, S. Takeda, H.B. Gu, and K. Yoshino, Chemistry Express 1(11), 635–638, 1986.

Primary Examiner—Joseph L. Schofer
Assistant Examiner—Wu C. Cheng
Attorney, Agent, or Firm—Michael D. Bednarek

[57] ABSTRACT

Conjugated conductive polymers which are photo-responsive upon ultra-violet light or visible light irradiation are prepared from copolymerization of photo-responsive groups containing heterocyclic monomers and 3-substituted heterocyclic monomers with the substituent containing a flexible segment like an alkyl group, ethoxyl group or siloxane group. The conductivity of the polymer can be controlled reversibly by irradiation of light and so can be used in optical-electronic applications or a production of detectors.

3 Claims, 4 Drawing Sheets

PHOTO-RESPONSIVE CONDUCTIVE POLYMERS AND THE PROCESSES OF MAKING THE SAME

This application is a division of application Ser. No. 07/867,460 filed Apr. 13, 1992 U.S. Pat. No. 5,272,234.

BACKGROUND OF THE INVENTION

The present invention relates to a photo-responsive conductive polymer and the processes of making the same, and particularly to a copolymerization of the 3-substituted thiophene monomers containing photo-responsive group with 3-substituted thiophene monomers.

Conventionally, the conductivity of a conjugated conductive polymer is about $10^{-12}$–$10^{-9}$ s/cm before doping and about $10^0$–$10^5$ s/cm after doping. Most of the conductive polymers can not be dissolved in organic solvents or melt-processed due to the rigid conjugated bond. Therefore, the polymers should be introduced with flexible side chains such as long alkyl groups to make the polymer soluble in organic solvents and melt-processable. On the other hand, in order to control the conductivity of the polymers by external stimulation, a photo-responsive functional group should be introduced into the polymers.

However, there is no disclosure related to a conductive polymer with photo-chemically induced property. In the related organic compound, only the Japan National Industrial Chemistry Laboratory discloses the synthesis of an azobenzene group containing 7,7,8,8-tetracyanoquinodimethane (TCNQ) derivatives and the making of a Langmuir-Blodget film which can change its conductivity when irradiated with ultra-violet light; the variation range is about 35%. But the entire preparation process is so complicated. Furthermore, the film has poor mechanical strength due to its low molecular weight, and can be easily fractured.

SUMMARY OF THE INVENTION

It is therefore an object of the present invention to provide a photo-responsive conductive polymer having the characteristics of conductivity, photo-responsiveness and processability, and also soluble in organic solvents such as chloroform.

In order to achieve the object stated above, the present invention uses an azobenzene group which has the photo-responsive property to modify 3-substituted thiophene monomers. The photo-responsive 3-alkyl thiophene derivatives thus obtained are copolymerized with 3-substituted thiophene monomers with flexible side chain such as alkyl groups with carbon number of or more than four. The copolymers are soluble in organic solvent such as chloroform because of the presence of long alkyl group in the side chain. Also, the copolymers can be processed by solution casting to produce a flexible free-standing film. The azobenzene group, when irradiated with ultra-violet or visible light, can generate photoexcited hopping sites allowing an increase in electrical conductivity of the copolymer. Thus the introduce of azobenzene group can be used to control the conductivity of the copolymers upon irradiation of light. Since the copolymers of the present invention can be easily processed, and the film so produced has adequate mechanical properties and photo-responsive property, the copolymers can be used in optical-electronic applications or in the production of detectors.

DETAILED DESCRIPTION OF THE PRESENT INVENTION

The copolymer of the present invention which is produced from the copolymerization of an azobenzene group containing 3-substituted alkyl thiophene monomers and 3-alkyl thiophene monomers has the properties of electrical conductivity, solubility, as well as melt-processability. The most important property, however, is its responsiveness to ultra-violet light and visible light, there from the conductivity of the polymers can be controlled reversibly through ultra-violet light or visible light stimulation. In addition to the azobenzene group, other photo-responsive isomerization groups like 1,2-stilbene and 1,2-azomethine can also be used in the present invention since they can generate photoexcited hopping sites also by the light irradiation. According to the side chain effect on the poly(3-alkyl thiophene), the conductivity and solubility of poly(3-alkyl thiophene) with the carbon numbers 4 to 18 are quite similar (J. Phys. Chem., 1987, 91, 6706).

The process for preparing the photo-responsive conductive copolymers of the present invention is characterized by the synthesis of photo-responsive groups containing heterocyclic derivative monomers and 3-substituted heterocyclic derivative monomers with a flexible substituent like alkyl group, ethoxyl group or siloxane group. The polymer thus prepared has the structural formula of:

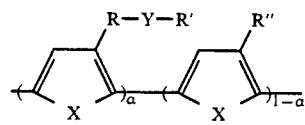

and the formulae of the monomers are:

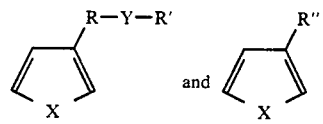

where X is S, NH or O;

R is —(CH$_2$)$_n$—, —(CH$_2$—CH$_2$—O)$_n$—, —(Si—O)$_n$—, —(CH$_2$)$_n$—O—,

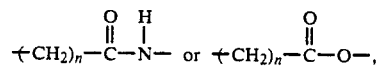

n is an integer from 1 to 12,

Y is

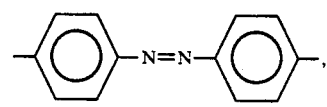

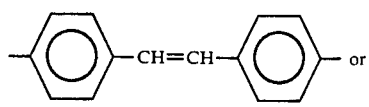

-continued

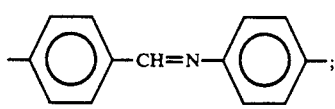

R' is —OCH$_3$, —CN, —NO$_2$, —H, —OH, —SO$_3$M, alkyl or —COOM, wherein M is H, Li, Na, K, Rb, Cs or Fr;

R" is —(CH$_2$)$_n$—CH$_3$, —(CH$_2$—CH$_2$—O)$_n$—CH$_3$, —(Si—O)$_n$—CH$_3$, wherein n is an integer from 3 to 21;

α is 0.05 to 1; and the polymer has a molecular weight of 10,000 to 1,000,000.

The monomers are placed in chloroform solvent under nitrogen flow at room temperature, and FeCl$_3$ or others transition metal halides like AlBr$_3$, AlCl$_3$, MoCl$_5$, WCl$_6$, NbCl$_5$, TaCl$_4$, TiCl$_4$, SnCl$_4$, BF$_3$ or ZnCl$_2$ are used as an oxidizing agent in the oxidation copolymerization.

The general procedure for the synthesis of the azobenzene containing 3-substituted thiophene monomers is described as follows. The chemical reaction formulae and reaction conditions are shown in example 1. The monomer is prepared by reflux of 3-(6-bromohexyl) thiophene) and 4-hydroxy-4'-methoxyazobenzene with a mole ratio of 1:1 in high purity acetone solution for two days at 60° C., using potassium carbonate and potassium iodide as catalysts; and then a solid is obtained. The solid is dissolved in dichloromethane and then filtered by silica gel column, after that, the solution is crystallized by ethanol to purify the compound, and 3-{6-[4-(4'-methoxyphenylazo) phenyloxy]hexyl} thiophene is obtained. The preparation of 3-(6-bromohexyl) thiophene refers to Angew. Chem. Int. Ed. Engl., 1990, 29, 419, and the preparation of 4-hydroxy-4'-methoxyazobenzene refers to Collect. Czech. Chem. Commun., 1969, 34, 2982. 3-hexylthiophene is prepared from couple reaction of 3-bromothiophene with the Grignard reagent hexylmagnesium bromide in the presence of the catalyst bis(1,3-diphenyphosphinopropane) nickel chloride, followed with a purification step by distillation at reduced pressure.

The synthesis procedure for the copolymers of the present invention is described as follows. A mixture of 10–25% of azobenzene containing 3-substituted thiophene derivative and 3-alkyl thiophene is dissolved in chloroform. Under a nitrogen stream, ferric chloride is added dropwisely into the chloroform solution, then the solution is stirred for 1 day at room temperature. The solution is poured into methanol and a precipitate is obtained. The precipitate is placed in a Soxhlet extractor for extraction with methanol and acetone successively for 1 day. After vacuum drying, the product is dissolved in chloroform, and then poured into a Teflon mold under a nitrogen stream at room temperature to produce a cast film with a thickness of about 20 to 100 μm. The film is stable in air and can retain its photoresponsive characteristic in air at room temperature.

This and other objectives of the invention as well as more complete understanding thereof maybe obtainable from the following specific examples with accompanying figure, wherein.

Figure 1:
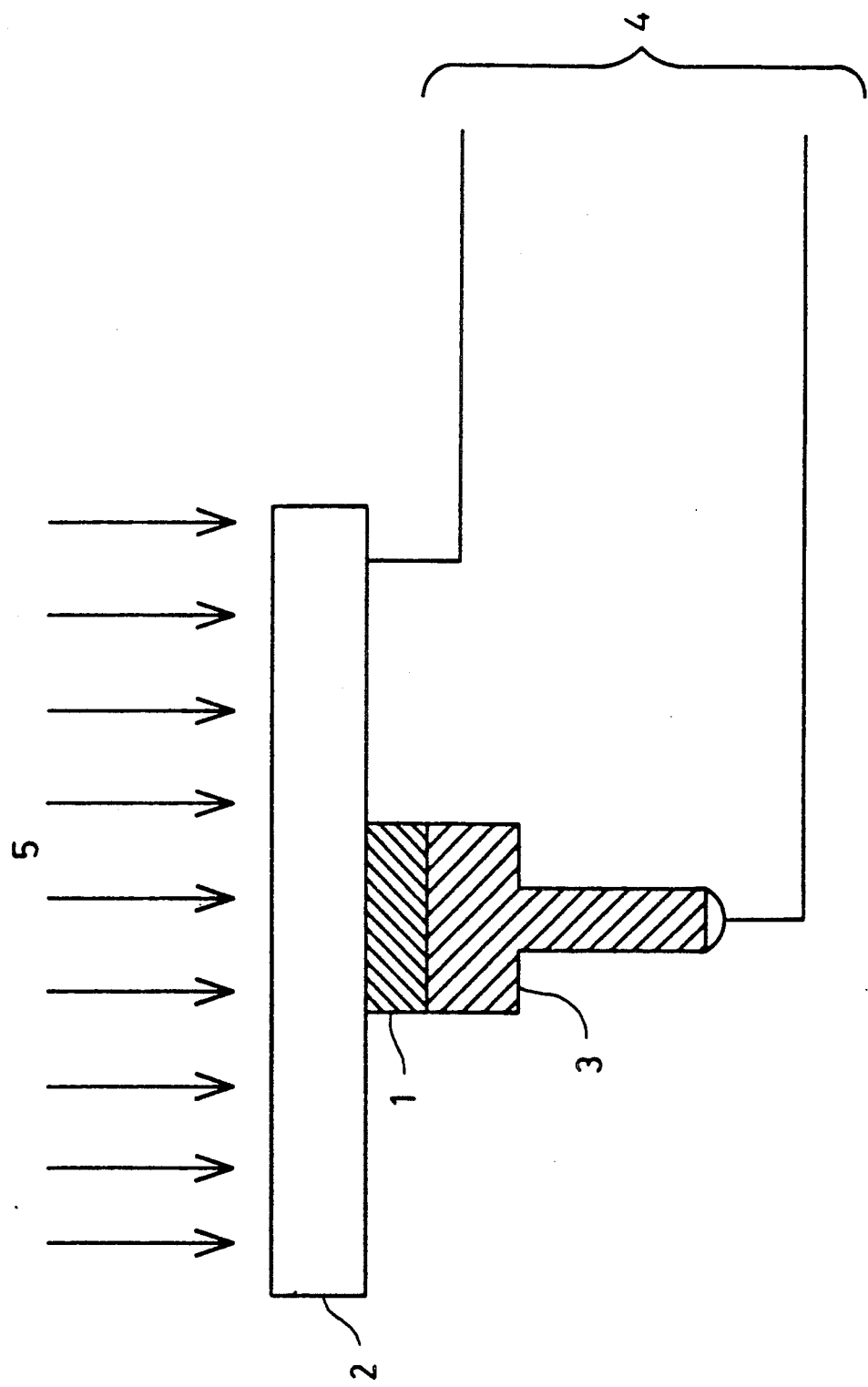
FIG. 1 is the structure of the testing device for measuring conductivity of the photo-responsive conductive polymers.

EXAMPLE 1: THE PREPARATION OF THE AZOBENZENE GROUP CONTAINING 3-ALKYL THIOPHENE DERIVATIVE MONOMERS

Synthesis 1: 3-hexylthiophene (ref: Tetrahedron, 1982, 38, 3347)

0.125 mole of n-hexylbromide was dissolved in 40 ml of ethyl ether. Then, 10 ml of ethyl ether was added in drops and also 0.13 mole of magnesium chip was added. The mixture was refluxed for 5 to 6 hours and the Grignard agent was obtained. The Grignard reagent was added to a solution consisting of 70 mg of NiDPPPCl$_2$ and 0.106 mole of 3-bromo thiophene in drops at 0° C., then the mixture was refluxed for 12 to 15 hours. After that, the mixture was hydrolyzed with 40 ml of 1N hydrochloric acid and 150 ml of ice water. Then, ethyl ether was used to extract the mixture for a few times, and the mixture was washed with water until the solution was neutral. The extract was dried by sodium sulfate to remove the solvent. The product of 3-hexylthiophene was obtained with a yield of 65% after distillation under reduced pressure.

Synthesis 2: 3-azobenzenealkyl thiophene derivatives (The reaction steps are shown in table I)

(i) 4-(4'-methylphenoxy)hexyl bromide (ref: J. Chem. Soc. 1958, 3303)

A solution of 62 g of methoxy phenol in 50 ml of methanol was added into a solution of 33.75 g of potassium hydroxide in 100 ml of methanol. The resulting solution was added dropwisely and slowly into 1 mole of α, -dibromohexane in 200 ml of acetone within 1 hour. After a reflux of the mixture for 1 hour, the mixture was concentrated and then diluted with water. The oil layer of the mixture was extracted with ethyl ether. Then, the ethyl ether layer was filtered and the filtrate was extracted with water. The solution was dried by calcium chloride, and 4-(4'-methoxyphenoxy) hexylbromide (compound 1, with a yield of 62%) was obtained by distillation under reduced pressure.

(ii) 3-[ω-(4-methoxyphenoxy) hexyl] thiophene

Using the Grignard cross couple reaction procedure as in synthesis 1, compound 1 and 3-bromothiophene were coupled to give 3-[-(4-methoxyphenoxy) hexyl] thiophene. Compound 2 was obtained after recrystallization with methanol, and the yield was 45%.

(iii) 3-(ω-bromoalkyl)thiophene (ref:Synthesis, 1983, 249)

0.12 moles of 48% hydrobromic acid and 0.198 moles of acetic anhydride were mixed and added dropwisely into 0.02 moles of compound 2 under a nitrogen stream. The mixture was refluxed for 20–25 hours at 100° C., and then diluted with water. After the mixture was extracted with ethyl ether, the organic layer was extracted with saturated sodium hydrogen carbonate aqueous solution until the filtrate was neutral. The organic layer was dried with sodium sulfate, and then concentrated to remove the solvent and added with a mixed solvent of n-hexane/ethyl ether. The solution was filtered and the filtrate was transferred into a short silica-gel column for an elution, using n-hexane as the elution solvent. After the separation, the solvent was removed and 3-(-bromohexyl)thiophene was obtained (compound 3, with a yield of 60%).

(iv) 4-hydroxyl-4'-methoxyazobenzene (ref:Collect.Czech. Chem. Commun., 1969, 34, 2982)

0.1 moles of p-methoxy aniline was dissolved in 28 ml of concentrated hydrochloric acid and 28 ml of water was added. Then 0.1 moles of sodium nitrite was dissolved in 350 ml of water and the solution was dropped slowly at 0°-5° C. into the aforementioned solution. 10 g of phenol, 4 g of sodium hydroxide and 21 g of sodium carbonate were dissolved in 350 ml of water and then added dropwisely into the above cold mixed solution at 0°-5° C. After 15 minutes, hydrochloric acid with a pH at 2-3 was added and the precipitate was washed twice with 50 ml of water. Compound 4, 4-hydroxyl-4'-methoxyazobenzene, was obtained with a yield of 82% after filtration and recrystallization with chloroform.

(iv') 4-(4'-hydroxylazobenzene) benzonitrile (ref: Makromol. Chem., 1984, 185, 1327)

Diazonium salt was prepared from aminobenzonitrile and sodium nitrite by using the method described in step (iv). The same amount of phenol and sodium hydroxide were dissolved in 250 ml of water, the solution was then added to the cold diazonium salt solution. The mixture was stirred for 1 hour at room temperature, and the precipitate was obtained by filtration and washed with water. The precipitate was dissolved again in a volume ratio of 1:1 ethanol aqueous solution, and acidified by adding hydrochloric acid dropwisely. The precipitate was filtered out and dried, the product 4-(4'-hydroxylazobenzene benzonitrile) was obtained (compound 4') with a yield of 78%.

(v) 3-{6-[4-(4'-methoxybenzoazo)phenoxy]hexyl}thiophene (ref: Makromol. Chem., Rapid Commun., 1986, 7,389)

16 mg of potassium carbonate and small amount of potassium iodide were added to 1.7 mmol of compound 3 and compound 4 (or compound 4'), and then dissolved in 30 ml of dried acetone. The solution was under reflux for 2 days at 60° C., and then was filtered and the solvent was evaporated. The residue was again dissolved in dichloro methane. After the solution was filtered by silica-gel followed by removal of solvent and recrystallization with ethanol, the product thus obtained was 3-azobenzenehexyl thiophene derivatives (for compound 5, the yield was 61%, and for compound 5', it was 72%).

TABLE 1

(i)
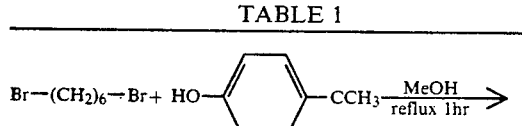

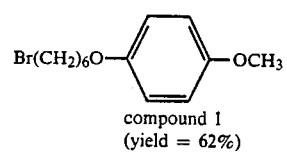
compound 1 (yield = 62%)

(ii)
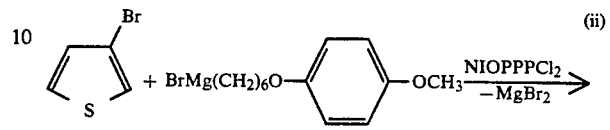

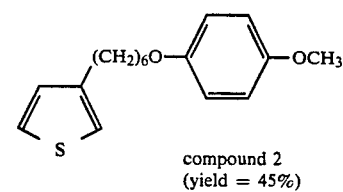
compound 2 (yield = 45%)

(iii)
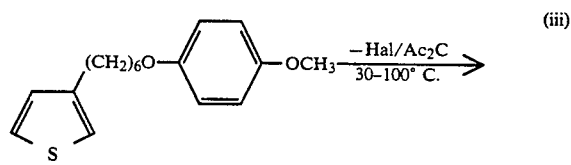

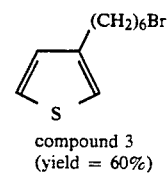
compound 3 (yield = 60%)

(iv)
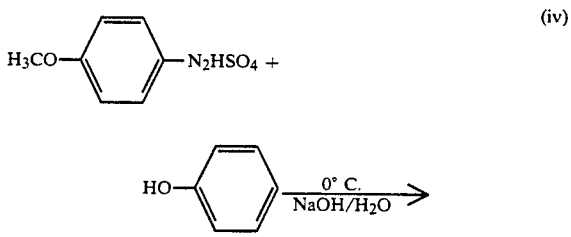

compound 4 (yield = 82%)

(iv')
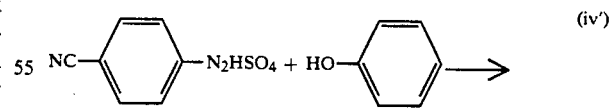

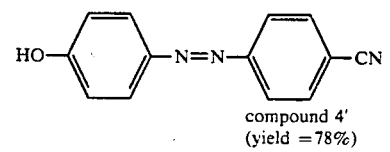
compound 4' (yield = 78%)

(v)
+

TABLE 1-continued

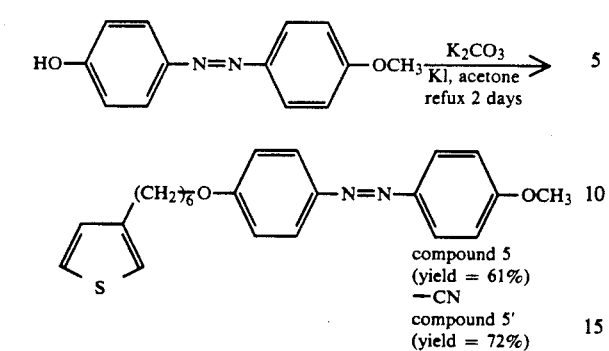

compound 5 (yield = 61%)
—CN
compound 5' (yield = 72%)

The structural analysis and the physical properties of the compounds mentioned in the example are summarized as below:

(1) 3-hexyl thiophene

Colorless liquid, boiling pt.=50°-51° C./0.15 torr., $^1$H NMR (400 MHz, CDCl$_3$, TMS standard) $\delta$=0.81 (dd, 3H; H-6), 1.18–1.22 (m, 2H;H-5), 1.23–1.27 (m, 4H;H-3,4), 1.53 (m, 2H;H-2), 2.54 (t, 2H;H-5), 6.83 (dd, 1H;H-2'), 6.84 (dd, 1H;H-4'), 7.13 (dd, 1H;H-5'), Mass M+=168.

(2) compound 5

Brown color powder, melting pt.=66° C., $^1$H NMR(400 MHz, CDCl$_3$, TMS standard) $\delta$=1.29–1.45 (m, 4H;H-3,4), 1.55 (m, 2H;H-5), 1.71 (m, 2H;H-2), 2.55 (t, 2H;H-6), 3.77 (s, 3H;OCH$_3$), 3.91 (t, 2H;H-1), 6.85 (dd, 1H;H-2'), 6.88 (dd, 1H;H-4'), 6.90 (d, 2H;H$_{Ph}$), 6.91 (d, 2H;H$_{Ph}$), 7.14 (dd, 1H;H-5'), 7.76 (d, 2H;H$_{Ph}$), 7.77 (d, 2H;H$_{Ph}$), Mass M+=394.

(3) compound 5'

Orange powder, melting pt.=117° C., $^1$H NMR (400 MHz, CDCl$_3$, TMS standard) $\delta$=1.32–1.53 (m, 4H;H-3,4), 1.61 (m, 2H;H-5), 1.77 (m, 2H;H-2), 2.59 (t, 2H;H-6), 3.98 (t, 2H;H-1), 6.87 (dd, 1H;H-2'), 6.93 (dd, 1H;H-4'), 6.95 (d, 2H;H$_{Ph}$), 7.17 (dd, 1H;H-5'), 7.72 (d, 2H;H$_{Ph}$), 7.85 (d, 2H;H$_{Ph}$), 7.88 (d, 2H;L H$_{Ph}$), Mass M+=389.

EXAMPLE 2: THE PREPARATION OF THE POLYMERS

A 250 ml three-necked flask was filled with 100 ml of chloroform solvent and 0.4M ferric chloride as an oxidizing agent. Under a stream of nitrogen gas, 20 ml of chloroform solution containing 0.01M of compound 5 and 0.09M of 3-hexyl thiophene were added dropwisely and slowly. Polymerization was carried out by stirring the solution for 1 day at room temperature under a stream of nitrogen gas. The polymer so obtained was precipitated out in methanol, and then the precipitate was extracted with methanol and acetone successively for 1 day to remove the residue of oxidizing agent and oligomer. The precipitate was dissolved in chloroform. After filtration, the filtrate was concentrated and then placed in a Teflon mold to produce a cast film. The film was then dried in vacuum until constant weight was obtained. The film thus prepared was a dark red free standing film with metallic luster, Tg (the glass transition temperature) is 12.9° C., $\overline{Mw}$ (weight average molecular weight) is 80,000 and $\overline{Mw}/\overline{Mn}$ is 4.3.

EXAMPLE 3

Figure 2:
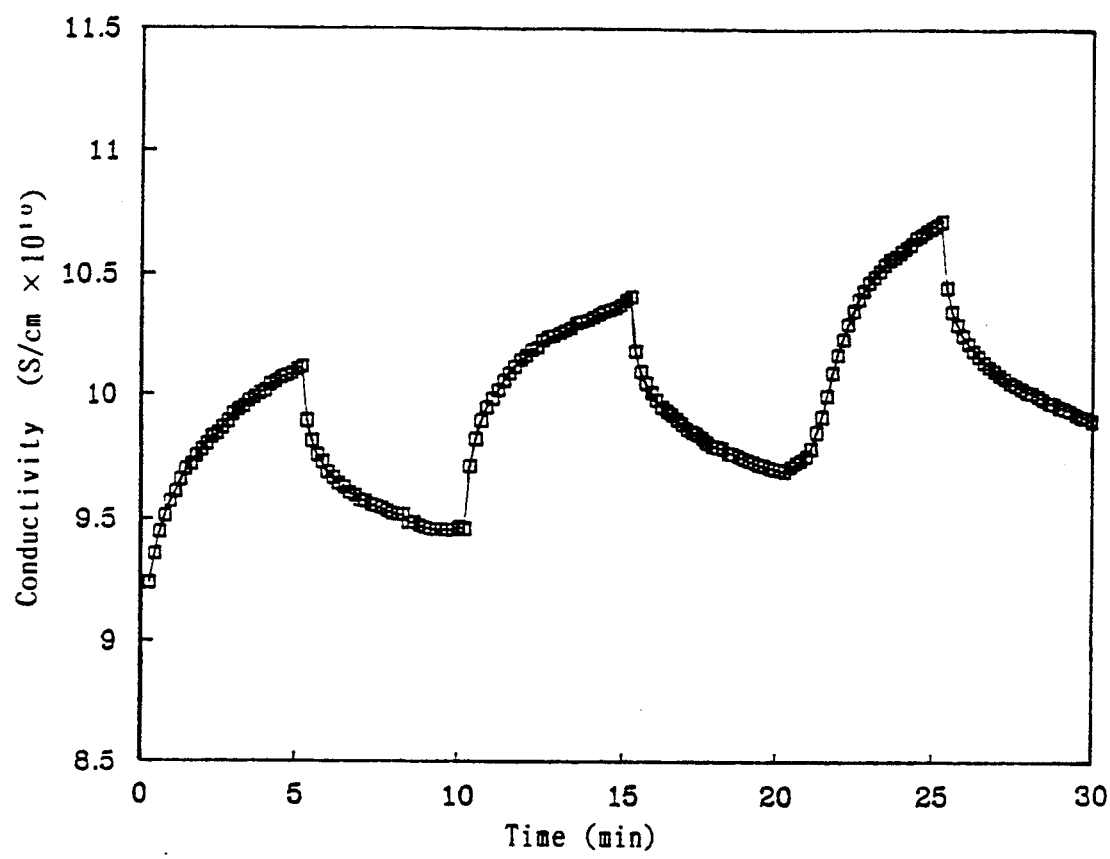
FIG. 2 is the variation of conductivity of the polymers before and after irradiation according to example 3.

According to FIG. 1, the free-standing film (about 60 μm in thickness) obtained in example 2 was sandwiched in between the transparent conductive glass 2 and copper electrode 3, and the exposure area was about 0.7 cm$^2$, the conductive glass 2 and copper electrode 3 were connected with a copper wire. A UV light of long wavelength (UVP BLAK-RAY 100 W, 360 nm) irradiated through the transparent glass for 5 minutes, then in dark for 5 minutes, and this step was repeated for three times. The conductivity was measured and the result is shown in FIG. 2. As shown in FIG. 2, the conductivity increased by about 18% under UV-irradiation and decreased in the dark. The variation in conductivity was reversible. Furthermore, the conductivity variations at the initial periods are very sharp when the UV light was on and off.

It is to be noted that the increase in conductivity during the UV irradiation is not due to the trans-cis isomerization, since an irradiation with visible light also generated the same result as to be revealed in example 5. Indeed, it can be attributed to a generation of photoexcited hopping sites in the azobenzene moiety upon irradiation of UV or visible light.

EXAMPLE 4

Figure 3:
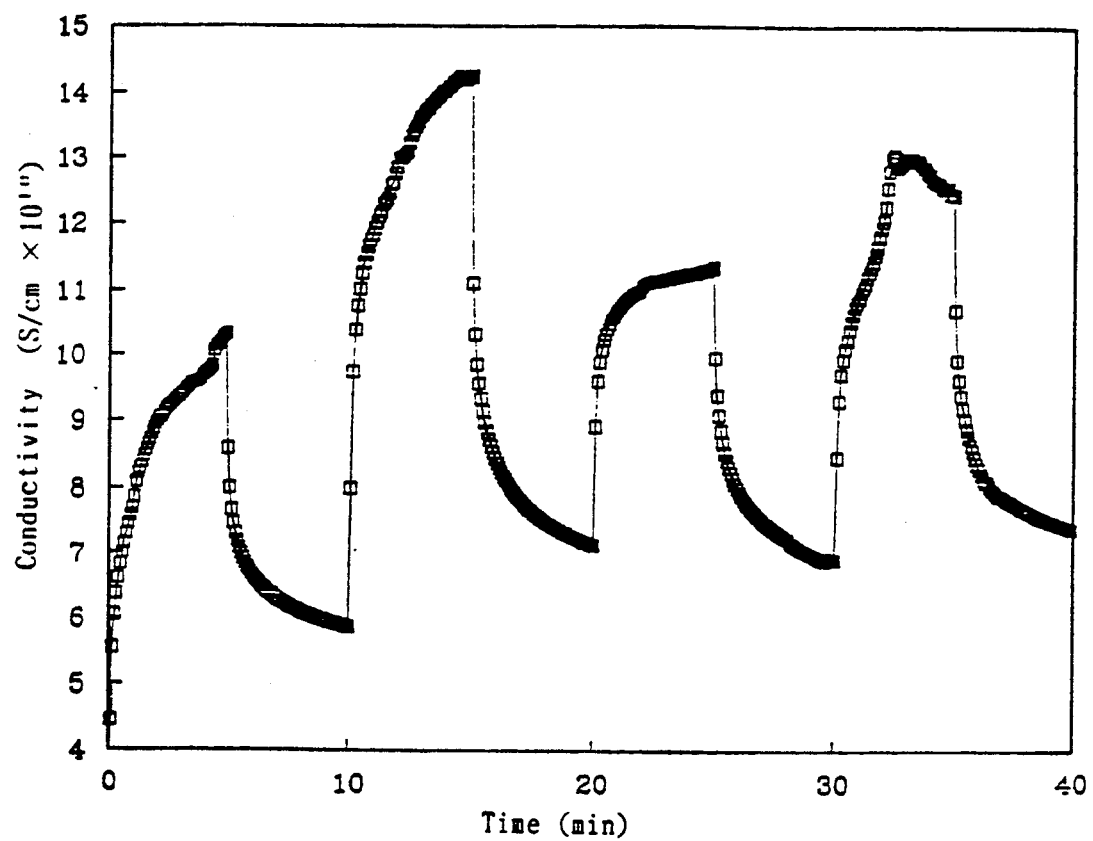
FIG. 3 is the variation of conductivity of the polymers before and after irradiation according to example 4.

The device used was the same as in example 3, and the content of azobenzene derivatives in the copolymer was 25 mole % (Tg=34.5° C., $\overline{Mw}$=100,000, $\overline{Mw}/\overline{Mn}$=3.6). The film was about 20 μm thick and was flexible and extensible but slightly stiffer than that in example 3. The variation of conductivity is shown in FIG. 3 and the maximum increase in conductivity is about 150%. Again, the conductivity variations at the initial periods are very sharp when the UV light was on and off.

EXAMPLE 5

Figure 4:
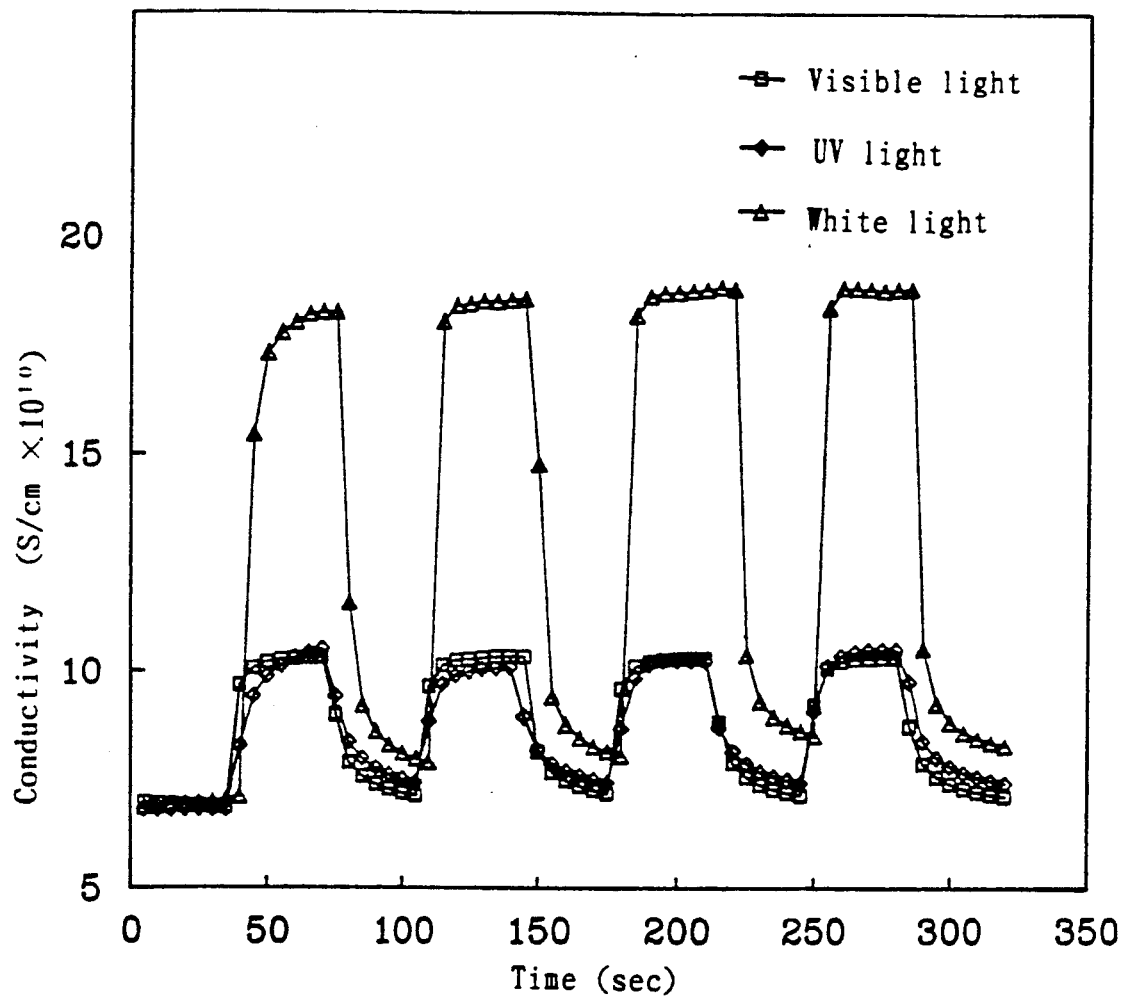
FIG. 4 is the variation of conductivity of the polymers before and after irradiation according to example 5.

The photo-responsive conductive polymer prepared as the procedure of example 2 (containing 25 mole % of compound 5', Tg=36.9° C., weight average molecular weight Mw=170,000, Mw/Mn=16) was cast into thin film with the thickness about 60 μm. The variations of conductivity upon UV light ($\lambda$=365 nm), visible light ($\lambda$>400 nm) and white light (from the source of 100 w Hg-lamp without filter), are shown in FIG. 4. It is shown that upon the irradiation of UV light and visible light, the conductivity increases by about 60% and 160% respectively. This example clearly indicated that the increase in conductivity upon light irradiation is not resulted from an isomerization of the azobenzene moiety, since no isomerization occurs upon irradiation with visible light.

While the preferred embodiments has been described, variations thereto will occur to those skilled in the art within the scope of the present invention concepts which are delineated by the following claims.

We claim:

1. A process for producing a photo-responsive conductive polymer, which comprises:
   (a) dissolving a photo-responsive group containing monomers with a structural formula of

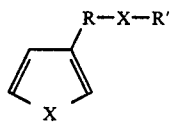

and monomers with a structural formula of

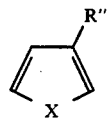

in a solvent; wherein X is selected from the group consisting of S, NH and O;

R is selected from the group consisting of —(CH$_2$—)$_n$—, —(CH$_2$—CH$_2$—O)$_n$—, —(Si—O)$_n$—, —(CH2)$_n$—O—,

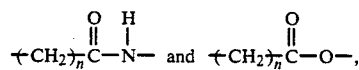

wherein n is an integer from 1 to 12,

Y is selected from the group consisting of

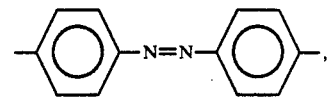

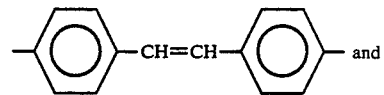

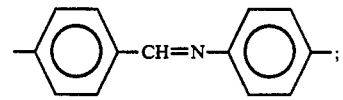

R' is selected from the group consisting of —OCH$_3$, —CN, —NO$_2$, —H, —OH, —SO$_3$M, alkyl and —COOM, wherein M is selected from the group consisting of H, Li, Na, K, Rb, Cs and Fr;

R" is selected from the group consisting of —(CH2—)$_n$—CH$_3$, —(CH$_2$—CH$_2$—O)$_n$—CH$_3$, —(Si—O)$_n$—CH$_3$, wherein n is an integer from 3 to 21;

(b) adding an oxidizing agent to said solution.

2. A process as claimed in claim 1, wherein said oxidizing agent is selected from the group consisting of FeCl$_3$, AlBr$_3$, AlCl$_3$, MoCl$_5$, WCl$_6$, NbCl$_5$, TaCl$_4$, TiCl$_4$, SnCl$_4$ and BF$_3$.

3. A process as claimed in claim 2, wherein said oxidizing agent is FeCl$_3$.

* * * * *